United States Patent
Jäger et al.

(10) Patent No.: US 11,168,341 B2
(45) Date of Patent: Nov. 9, 2021

(54) METHOD FOR PRODUCING AMINOBENZOIC ACID OR AN AMINOBENZOIC ACID DERIVATIVE

(71) Applicant: COVESTRO DEUTSCHLAND AG, Leverkusen (DE)

(72) Inventors: Gernot Jäger, Cologne (DE); Wolfgang Beckmann, Berlin (DE); Amgad Salah Moussa, Bad Säckingen (DE); Guenter Olf, Zülpich (DE); Guido Becker, Krefeld (DE); Hasan Akyildiz, Duisburg (DE); Andreas Damm, Wermelskirchen (DE); Thomas Hamedinger, Leverkusen (DE); Wolf Kloeckner, Cologne (DE); Swantje Behnken, Sacramento, CA (US)

(73) Assignee: Covestro Deutschland AG, Leverkusen (DE)

( * ) Notice: Subject to any disclaimer, the term of this patent is extended or adjusted under 35 U.S.C. 154(b) by 216 days.

(21) Appl. No.: 15/776,113

(22) PCT Filed: Nov. 17, 2016

(86) PCT No.: PCT/EP2016/077963
§ 371 (c)(1),
(2) Date: May 15, 2018

(87) PCT Pub. No.: WO2017/085170
PCT Pub. Date: May 26, 2017

(65) Prior Publication Data
US 2018/0334694 A1 Nov. 22, 2018

(30) Foreign Application Priority Data

Nov. 20, 2015 (EP) .................................. 15195527

(51) Int. Cl.
*C12P 13/00* (2006.01)
*C12P 13/04* (2006.01)
(Continued)

(52) U.S. Cl.
CPC .............. *C12P 13/005* (2013.01); *C12N 1/00* (2013.01); *C12N 1/20* (2013.01); *C12N 1/205* (2021.05);
(Continued)

(58) Field of Classification Search
CPC .......... C12P 13/005; C12P 13/04; C12N 1/20; C12N 1/00
See application file for complete search history.

(56) References Cited

U.S. PATENT DOCUMENTS

| 4,851,570 A | 7/1989 | Zaby et al. |
| 5,053,539 A | 10/1991 | Yano et al. |

(Continued)

FOREIGN PATENT DOCUMENTS

| JP | 04-330290 A | 11/1992 |
| JP | 05000094 A * | 1/1993 |

(Continued)

OTHER PUBLICATIONS

Kumar et al., Cryst. Growth Des., 2014, 14:1865-1881 (Year: 2014).*

(Continued)

*Primary Examiner* — Allison M Fox
*Assistant Examiner* — Qing Xu
(74) *Attorney, Agent, or Firm* — N. Denise Brown; Donald R. Palladino (57) ABSTRACT

The invention relates to a method for producing aminobenzoic acid or a aminobenzoic acid derivative via the fermentation of a suitable raw material under the influence of suitable microorganisms and obtaining a fermentation broth (Continued)

containing aminobenzoate and/or aminobenzoic acid. In particular, the invention relates to the step of obtaining the aminobenzoic acid from the fermentation broth, wherein the crystallisation of aminobenzoic acid is carried out via a simple one-stage acid treatment in the presence of seed crystals. The aminobenzoic acid crystallised in this simple manner can be easily separated from the mother liquor, further cleaned if necessary, and then supplied to the different applications.

14 Claims, 3 Drawing Sheets

(51) Int. Cl.
  C12N 1/20 (2006.01)
  C12N 1/00 (2006.01)
  *C12R 1/15* (2006.01)
  *C12R 1/19* (2006.01)
  *C12R 1/40* (2006.01)
(52) U.S. Cl.
  CPC .......... *C12P 13/04* (2013.01); *C12R 2001/15* (2021.05); *C12R 2001/19* (2021.05); *C12R 2001/40* (2021.05)

(56) References Cited

U.S. PATENT DOCUMENTS

| | | |
|---|---|---|
| 5,286,760 A | 2/1994 | Bolton et al. |
| 7,230,130 B2 | 6/2007 | Ströfer et al. |
| 7,253,321 B2 | 8/2007 | Hagen et al. |
| 7,547,801 B2 | 6/2009 | Pohl et al. |
| 8,079,752 B2 | 12/2011 | Rausch et al. |
| 8,097,751 B2 | 1/2012 | Koch et al. |
| 8,178,322 B2 | 5/2012 | Araki et al. |
| 2017/0066713 A1 | 3/2017 | Jaeger et al. |
| 2017/0152535 A1 | 6/2017 | Jaeger et al. |

FOREIGN PATENT DOCUMENTS

| | | | |
|---|---|---|---|
| JP | 2013230993 A | * | 11/2013 |
| WO | WO 2015/124687 A1 | * | 8/2015 |

OTHER PUBLICATIONS

Zeng et al., Hydrometallurgy, 2007, 89:107-116. (Year: 2007).*
Bredol et al., J. Material Sci, 1998, 33:471-476. (Year: 1998).*
Balderas-Hernandez, V. E. et al., "Metabolic engineering for improving anthranilate synthesis from glucose in *Escherichia coli*", Microb. Cell. Fact. 2009, 8, 19 (doi: 10.118611475-2859-8-19).
S. Gracin et al., Crystal Growth & Design, 2004, 4, 1013-1023.
Zapala et al., Biophys. Chem., 140 (1-3) (2009) 91-98.
Beckmann, Crystallization, Wiley 2013, pp. 175 to 176.
Beckmann, Crystallization, Wiley 2013, pp. 203 to 233.
Ojala, W. H.; Etter, M. C., J. Am. Chem. Soc. 1992, 114, 10288-10293.
Bhavana Guptaa et al., Polymers Advanced Technologies, 2011, 22, 1982-1988.
Wiklund et al., Current Organic Synthesis, 2006, 3, 379-402.

* cited by examiner

METHOD FOR PRODUCING AMINOBENZOIC ACID OR AN AMINOBENZOIC ACID DERIVATIVE

CROSS-REFERENCE TO RELATED APPLICATIONS

This application is a national stage application under 35 U.S.C. § 371 of PCT/EP2016/077963, filed Nov. 17, 2016, which claims the benefit of European Application No. 15195527.5, filed Nov. 20, 2015, both of which are being incorporated by reference herein.

FIELD

The present invention relates to a process for preparing aminobenzoic acid or an aminobenzoic acid derivative by fermentation of a suitable raw material under the influence of suitable microorganisms to obtain an aminobenzoate- and/or aminobenzoic-acid-comprising fermentation broth. More particularly, the present invention relates to the step of gaining the aminobenzoic acid from the fermentation broth, wherein the crystallization of aminobenzoic acid is carried out by a mere one-step acid treatment in the presence of seed crystals. The aminobenzoic acid thus crystallized in a simple manner can be easily removed from the mother liquor, further purified if necessary, and then supplied to a wide variety of different intended applications.

BACKGROUND

The fermentative preparation of aminobenzoic acid or of products which can be obtained by further chemical conversion of aminobenzoic acid (hereinafter aminobenzoic acid derivatives) is described in the literature. For the fermentative preparation of aminobenzoic acid, reference may be made by way of example to Balderas-Hernandez, V. E. et al., "Metabolic engineering for improving anthranilate synthesis from glucose in *Escherichia coli*", *Microb. Cell. Fact.* 2009, 8, 19 (doi: 10.118611475-2859-8-19). In the patent literature, too, there are publications in relation thereto; see, for example, WO 2015/124686 A1 and WO 2015/124687 A1 and also the literature respectively cited therein. Products which can be obtained by further chemical conversion of aminobenzoic acid are described by Wiklund et al. (Per Wiklund et al., *Current Organic Synthesis*, 2006, 3, 379 402).

Other acids too, such as L-amino acids or nucleic acids, have already been prepared by fermentation, as described in EP 2 130 924 A1. In the process described therein, the desired product already precipitates in the fermentation broth, meaning that it is possible to dispense with a separate crystallization step. Optionally, seed crystals are added during the fermentation.

In S. Gracin et al., *Crystal Growth & Design*, 2004, 4, 1013 1023, the polymorphism and the crystallization of para-aminobenzoic acid are discussed. The paper does not go into specifics in the case of the isolation of para-aminobenzoic acid from fermentation broths. The isolation of a target compound from a fermentation broth is, however, anything but trivial. It can comprise a series of steps such as extraction, filtration, adsorption or crystallization. It is even possible that all these steps are necessary in order to obtain the desired target compound in a sufficient purity. However, each of these steps inevitably causes additional effort and thus costs. In addition, the lower the yield of the target compound, the more steps for their isolation that are necessary. Therefore, it is generally desirable to minimize the number of steps up to the isolation of the target compound in the desired purity.

Fermentation processes generally proceed in an aqueous environment. It is therefore especially desirable to be able to isolate the fermentation-prepared target compound directly from said aqueous environment and, for instance, to be able to dispense with a removal by means of an organic solvent.

It is generally known that the solubility of ortho-aminobenzoic acid as amphoteric compound can be minimized by specific setting of the pH. The two $pK_a$ values are 2.2 and 4.9 (cf. Zapata et al., *Biophys. Chem.*, 140 (1-3) (2009) 91-98), corresponding to a solubility minimum at a pH of about 3.5.

It would therefore actually be expected that the isolation of ortho-aminobenzoic acid from fermentation broths should be possible without great effort. In complete contrast thereto, JP04-330290A describes a multistep process for isolating ortho-aminobenzoic acid, in which (1) optionally and preferably, by means of a pH adjustment of the fermentation broth to a pH from 4 to 6, proteins present in the fermentation broth are precipitated, (2) the biomass is removed from the fermentation broth (and this is thus "sterilized"), then (3) by means of a pH adjustment to a pH from 5 to 10 and subsequent adsorption to a suitable column, a decoloration is brought about, (4) the ortho-aminobenzoic-acid-containing solution is concentrated, before (5) even a start can be made to crystallize ortho-aminobenzoic acid by pH adjustment to the pH corresponding to the isoelectric point of ortho-aminobenzoic acid, whereupon lastly (6) the precipitated crystals are removed.

The process thus comprises two to three steps of pH adjustment and is therefore multistep with respect to the setting of the pH that is necessary for the crystallization. Furthermore, the ortho-aminobenzoic acid isolated in a complicated manner in five to six steps only has a purity of 94% and is also only obtained in a relatively low yield of 67% of the theoretically possible yield. The process is complex and requires a two-time to three-time pH change, this naturally being associated with an elevated salt load of the wastewaters. In addition, ortho-aminobenzoic acid is temperature-sensitive and can decarboxylize to form the aminobenzoic acid derivative aniline. The latter is itself problematic if aniline is the actual target product of the synthesis sequence, since a premature decarboxylation at this point can lead to losses in yield as a result of a comparatively high water-solubility of aniline at the relevant pH levels. A fastest possible isolation of the ortho-aminobenzoic acid at a lowest possible temperature is therefore desirable.

WO 2015/124687 A1 discloses on page 17 the gain of ortho-aminobenzoic acid (anthranilic acid) from a fermentation broth by addition of acid in a general manner, but does not teach any details relating to the exact configuration of this step.

SUMMARY

There was therefore a need for further improvements in the fermentative preparation of aminobenzoic acid or aminobenzoic acid derivatives, specifically especially in the step for the isolation of the aminobenzoic acid from the fermentation broth.

Meeting this need, the present invention provides a process for preparing aminobenzoic acid, especially ortho-aminobenzoic acid, or an aminobenzoic acid derivative, especially a derivative of the ortho isomer of the aminobenzoic acid, comprising the steps:

(I) fermentation of a raw material which comprises at least one fermentable carbon-containing compound and which is preferably selected from the group consisting of starch hydrolyzate, sugarcane juice and sugar beet juice by using microorganisms, wherein an aminobenzoate- and/or aminobenzoic-acid-comprising fermentation broth is obtained;

(II) optional pretreatment of the fermentation broth obtained in step (I), comprising
  (1) removal of the microorganism from the fermentation broth obtained in step (I) without pH adjustment, wherein a microorganism-depleted fermentation broth is obtained,
  and/or
  (2) decoloration of the fermentation broth obtained in step (I) or, when carrying out step (II)(1), of the microorganism-depleted fermentation broth obtained in step (II)(1), without pH adjustment;

(III) one-step treatment of the fermentation broth obtained in step (I) or step (II)(1) or step (II)(2) in a reactor with acid such that aminobenzoic acid is precipitated from the fermentation broth;

(IV) isolation of the aminobenzoic acid precipitated in step (III), wherein mother liquor remains;

(V) optional further purification of the aminobenzoic acid gained in step (IV), preferably by washing with water;

(VI) optional further conversion of the aminobenzoic acid obtained in step (IV) or step (V) to form an aminobenzoic acid derivative;

wherein step (III) is carried out such that seed crystals of aminobenzoic acid are present.

The acid treatment in step (III) is, in this connection, "one-step" in the sense that the desired target pH is directly set by addition of acid, without intermediate steps (such as filtration, centrifugation, column-chromatography treatment and the like) at pH levels between the starting pH (i.e., the pH of the fermentation broth obtained in step (I) or step (II)(1) or step (II)(2), depending on whether the optional step (II) is carried out and, if yes, of which substeps it consists) and the target pH (i.e., the pH which ensues after completed acid treatment in step (III)). The setting of the desired target pH by the described one-step acid treatment is therefore done only in step (III) of the process according to the invention. The fermentation broth obtained in step (I) is thus, according to the invention, either immediately subjected to step (III) or it is immediately subjected to step (II), and the process product of step (II) (i.e., the process product obtained in step (II)(1) or step (II)(2)) is then immediately subjected to step (III). "Immediately" means, in this connection, "without intermediate steps". In other words: step (II) consists of step (II)(1) and/or step (II)(2). Steps (II)(1) and (II)(2) are, according to the invention, carried out "without pH adjustment", i.e., without acid treatment. The multiplicity of pH adjustments (acid treatments) described in the prior art is, in the process according to the invention, therefore reduced to a single pH adjustment (acid treatment).

"Seed crystals" in the context of the present invention are understood to mean
  (i) crystals of aminobenzoic acid (which can also originate from an external source, for example can be additionally bought) that are initially charged in the reactor from step (III) and/or
  (ii) crystals of aminobenzoic acid that are formed in situ in the reactor from step (III) during continuous performance of this step and that serve as seed crystals for the precipitation of further aminobenzoic acid (so-called secondary seed formation), as will be explained in more detail further below.

The term "aminobenzoic acid derivative" means, in the context of the present invention, a product which is obtained by further chemical conversion of aminobenzoic acid.

The process according to the invention makes it possible to gain aminobenzoic acid in a simple manner in high purity. Generally, it is not necessary to recrystallize the aminobenzoic acid gained before its further use; preferably, step (V), if carried out, therefore does not comprise any recrystallization. The mother liquor remaining after step (IV) in the context of the process according to the invention contains aminobenzoic acid only in low amounts, preferably amounts not exceeding thermodynamic solubility. As a result, wastewater pollution is minimized The process according to the invention further allows the gain of aminobenzoic acid in such crystal sizes that, after removal of the mother liquor in step (IV) or, if carried out, after removal of the wash water in step (V), there ensues a residual moisture content which also allows a further use of the aminobenzoic acid without complicated drying processes.

DETAILED DESCRIPTION

Embodiments of the invention will be described in more detail below. In this connection, various embodiments can be combined with one another as desired, provided the general context does not reveal the opposite to a person skilled in the art.

Step (I) of the process according to the invention can be carried out according to any procedure known from the prior art. Particular preference is given to processes as described in WO 2015/124686 A1 and WO 2015/124687 A1 using bacteria as microorganisms. In this connection, reference is made in particular to WO 2015/124687 A1, (i) page 15, line 8 to page 16, line 30, (ii) example 1 (page 29, lines 4 to 26), (iii) example 3 (especially page 34, lines 10 to 18), (iv) example 4 (especially page 55, lines 9 to 31).

It is self-evident that the fermentative preparation of aminobenzoic acid requires not only a carbon source, but also a nitrogen source. If the fermentable carbon-containing compound to be used in step (I) does not already contain a suitable nitrogen-containing compound as nitrogen source, such a compound must be added. Preference is given, for this purpose, to the nitrogen-containing compound selected from the group consisting of ammonia gas, ammonia water, ammonium salts (especially ammonium sulfate and ammonium chloride) and urea.

Preferably, the microorganisms used in step (I) comprise a species selected from the group consisting of *Escherichia coli, Pseudomonas putida* and *Corynebacterium glutamicum*. Particularly preferably, the microorganisms consist only of representatives of exactly one of these species. *Corynebacterium glutamicum* ATTC 13032 is especially preferred in this connection.

The pH to be observed in the fermentation is determined by the microorganism used. The fermentation in step (I) is carried out especially at such a pH that a spontaneous precipitation of aminobenzoic acid as early as in the fermentation broth is largely to completely avoided, i.e., step (I) is carried out especially at a pH of ≥6.5. Microorganisms such as *Corynebacterium glutamicum, Pseudomonas putida* or *Escherichia coli* are preferably cultivated at substantially neutral pH levels (i.e., preferably at a pH in the range from 6.5 to 8.0).

In any case, the microorganism from step (I) is preferably selected such that, in the fermentation, the ortho isomer of aminobenzoic acid and/or aminobenzoate is formed (selectively). "Selectively" means, in this connection, that other isomers are not formed or at most in low-level proportions (i.e., in proportions as determined by high-performance liquid chromatography, HPLC—of altogether not more than 0.50%, preferably not more than 0.25%, very particularly preferably not more than 0.10%, extremely preferably not more than 0.05%, based in each case on the entirety of all aminobenzoic acid isomers). Suitable for this purpose are especially microorganisms of a species selected from the group consisting of *Escherichia coli, Pseudomonas putida* and *Corynebacterium glutamicum*.

To obtain a suitable bacterium, there are fundamentally two routes available, which can also be combined in a preferred configuration:
(i) The enzymatic reactions in the aminobenzoic acid metabolic pathway in the bacterial cell can be elevated such that aminobenzoic acid is produced more rapidly than it is consumed.
(ii) The follow-up reactions by means of which aminobenzoic acid is transferred to further metabolites or products (e.g., tryptophan) can be reduced or switched off, meaning that even the rate of aminobenzoic acid formation in wild-type strains is sufficient in order to lead to an accumulation of aminobenzoic acid in the cell.

Methods for gaining bacteria having the aforementioned properties are known in the prior art. Suitable bacteria can, for example, be identified by screening for mutants which release aminobenzoic acid into the surrounding medium. The targeted modification of key enzymes by means of gene-technology methods is, however, preferred. Using customary gene-technology methods, gene expression and enzyme activity can be enhanced, diminished or even completely prevented as desired. The result is recombinant strains.

Particularly preferably, the bacteria to be used in step (I) contain a modification of the anthranilate phosphoribosyltransferase activity, which modification reduces said enzyme activity. As a result of said modification, the conversion of ortho-aminobenzoate to N-(5-phospho-D-ribosyl)anthranilate is reduced or completely prevented. This brings about an accumulation of aminobenzoic acid in the cell. The term "anthranilate phosphoribosyltransferase activity" refers, in this connection, to an enzyme activity by means of which the conversion from ortho-aminobenzoate to N-(5-phospho-D-ribosyl)anthranilate is catalyzed.

In the bacterium *Corynebacterium glutamicum*, the anthranilate phosphoribosyltransferase activity is encoded by the trpD gene (cg3361, Cg13032, NCg12929). In the case of *Pseudomonas putida*, the encoding is achieved via the trpD gene (PP_0421) within the trpDC operon.

The described reduction in the anthranilate phosphoribosyltransferase activity can fundamentally be achieved in three ways:
(i) The regulation of the expression of the gene for the anthranilate phosphoribosyltransferase activity can be modified such that the transcription of the gene or subsequent translation is diminished or prevented.
(ii) The nucleic acid sequence of the gene for anthranilate phosphoribosyltransferase activity can be modified such that the enzyme which is encoded by the modified gene has a lower specific activity.
(iii) The native gene for anthranilate phosphoribosyltransferase activity can be replaced with another gene which originates from a different organism and encodes an enzyme having a specific anthranilate phosphoribosyltransferase activity which is lower than that of the aforementioned native genes (e.g., trpD or tipDC).

Irrespective of which microorganism is used, the fermentation broth at the start of the fermentation in step (I) comprises recombinant cells of the microorganism used and at least one fermentable carbon-containing compound (and also at least one nitrogen-containing compound as nitrogen source, either as constituent of the carbon-containing compound or added). Preferably, the fermentation broth additionally contains yet further constituents selected from the group consisting of buffer systems, inorganic nutrients, amino acids, vitamins and further organic compounds which are required for the growth or the housekeeping metabolism of the recombinant cells. The fermentation broth is water-based. After use of the fermentation process, the fermentation broth also comprises aminobenzoic acid and/or aminobenzoate (depending on the pH at which the fermentation is carried out), the intended fermentation product.

A fermentable carbon-containing compound in the context of the present invention is understood to mean any organic compound or mixture of organic compounds which can be used by the recombinant cells of the microorganism used in order to produce aminobenzoic acid. The production of aminobenzoic acid can, in this connection, take place in the presence or absence of oxygen.

Preference is given in this connection to those fermentable carbon-containing compounds which can additionally serve as energy and carbon source for the growth of the recombinant cells of the microorganism used. Particularly suitable are starch hydrolyzate, sugarcane juice, sugar beet juice and hydrolyzates from lignocellulose-containing raw materials. Likewise suitable are glycerol and C1 compounds, especially carbon monoxide.

In a preferred embodiment, step (I) is carried out continuously, i.e., that the reactants are continuously fed to the fermentation reactor and the product is continuously withdrawn from the fermentation reactor. In a continuous procedure, the microorganism is, if need be, outputted with the product stream; however, the microorganism generally reproduces itself, meaning that a feeding of fresh microorganism is generally not necessary (but can of course be performed if necessary). A retention of cells in order to avoid the output of microorganism is likewise possible.

In another preferred embodiment, step (I) is carried out in a discontinuous procedure (so-called "batch mode"). In one variant of the discontinuous mode (so-called "fed batch mode"), the reactants are fed to the fermentation reactor in a continuous manner or at intervals, preferably in a continuous manner, for as long as it is allowed by the reactor volume, without products being withdrawn from the reactor. The reaction is interrupted after addition of the maximum possible amount of reactants and the product mixture is withdrawn from the fermentation reactor.

Irrespective of the exact mode, the reaction apparatus in which step (I) is carried out (hereinafter fermentation reactor) preferably comprises devices for the measurements of important process parameters such as temperature, pH of the fermentation broth, concentration of substrate and product, level of dissolved oxygen, cell density of the fermentation broth. Especially preferably, the fermentation reactor comprises devices for the adjustment of at least one (preferably of all) of the aforementioned process parameters.

Suitable fermentation reactors are stirrer tanks, membrane reactors, plug flow reactors or loop reactors (see, for example, Bioprozesstechnik [Bioprocess technology], Horst Chmiel, ISBN-10: 3827424763, Spektrum Akademischer Verlag). Particularly preferred both for aerobic and for anaerobic fermentations are stirrer-tank reactors and loop reactors (especially airlift reactors, in which the circulation of the liquid in the reactor is achieved by supply of gas).

The optional step (II)(1), the removal of the microorganism from the fermentation broth, is known per se from the prior art and is achieved in the context of the present invention especially by filtration or centrifugation. Preferably, said step, if done, is carried out as described in WO 2015/124686 A1 and WO 2015/124687 A1. In this connection, reference is made in particular to WO 2015/124687 A1, page 15, line 8 to page 15, line 17.

The optional step (II)(2), which, if carried out, follows either step (I) or step (II)(1), is preferably carried out such that fermentation broth or microorganism-depleted fermentation broth is conducted across a column with tight packing in order to remove dyes by means of adsorption. As possible solid phase, it is possible for example to use kieselguhr or ion-exchange packing materials. Step (II)(2) is preferably carried out when fermentation broth from step (I) or (II)(1) contains those colored substances which could interfere with the subsequent crystallization.

In step (III) of the process according to the invention, the pH is set by addition of acid to the fermentation broth such that aminobenzoic acid crystallizes. This type of crystallization is also referred to as reactive crystallization. This is preferably done such that the pH of the resulting mixture corresponds to that of the isoelectric point of the isomer to be precipitated of aminobenzoic acid, or at least approaches it. In the case of ortho-aminobenzoic acid as desired product, the pH is therefore set preferably to a level in the range from 3.0 to 4.7, particularly preferably to a level in the range from 3.2 to 3.7, very particularly preferably to a level in the range from 3.4 to 3.6, i.e., close to or corresponding to the isoelectric point at pH 3.5. Said isoelectric point is, for the two other isomers of aminobenzoic acid, about pH 3.7 in each case.

Possible as acid are all acids by means of which it is possible to set a pH which corresponds to the isoelectric point of the desired aminobenzoic acid isomer or at least approaches it. Preference is given, for this purpose, to using strong mineral acids, more particularly hydrochloric acid, sulfuric acid and/or phosphoric acid. Preferably, the acid used in step (III) comprises hydrochloric acid, particularly preferably hydrochloric acid of a concentration from 15% by mass to 37% by mass, very particularly preferably hydrochloric acid of a concentration from 18% by mass to 25% by mass. It is especially preferred that the acid does not comprise, besides said hydrochloric acid, any further acid (i.e., no further acid is added from an external source) with the exception of optionally added recycled mother liquor from step (IV). If a mixture of hydrochloric acid and a portion of the mother liquor obtained in step (IV) is used as the acid used in step (III), preference is given to mixing 1.0% by mass to 50% by mass of the mother liquor obtained altogether in step (IV) with hydrochloric acid.

Figure 1:
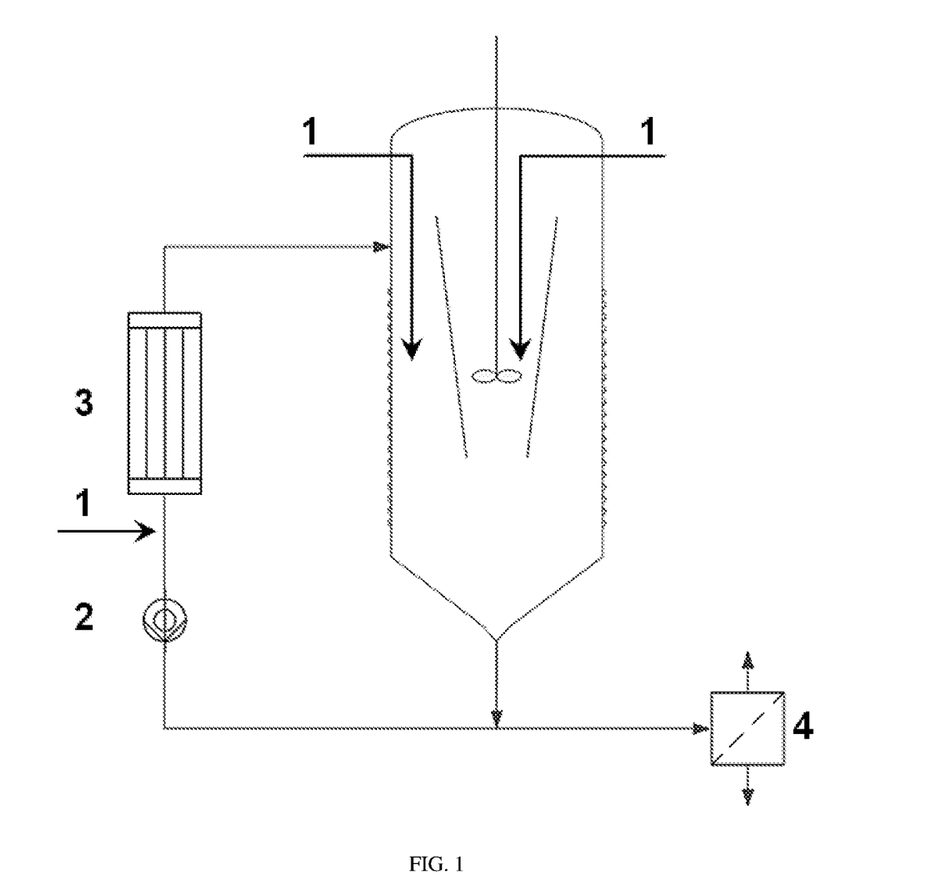
FIG. 1 illustrates a crystallizer with forced circulation crystallization without fittings. This crystallizer comprises (1) feeding devices for fermentation broth or acid, (2) a pump or crusher, (3) a heat exchanger, and (4) a solid/liquid separation (e.g. filtration) system.
Figure 2:
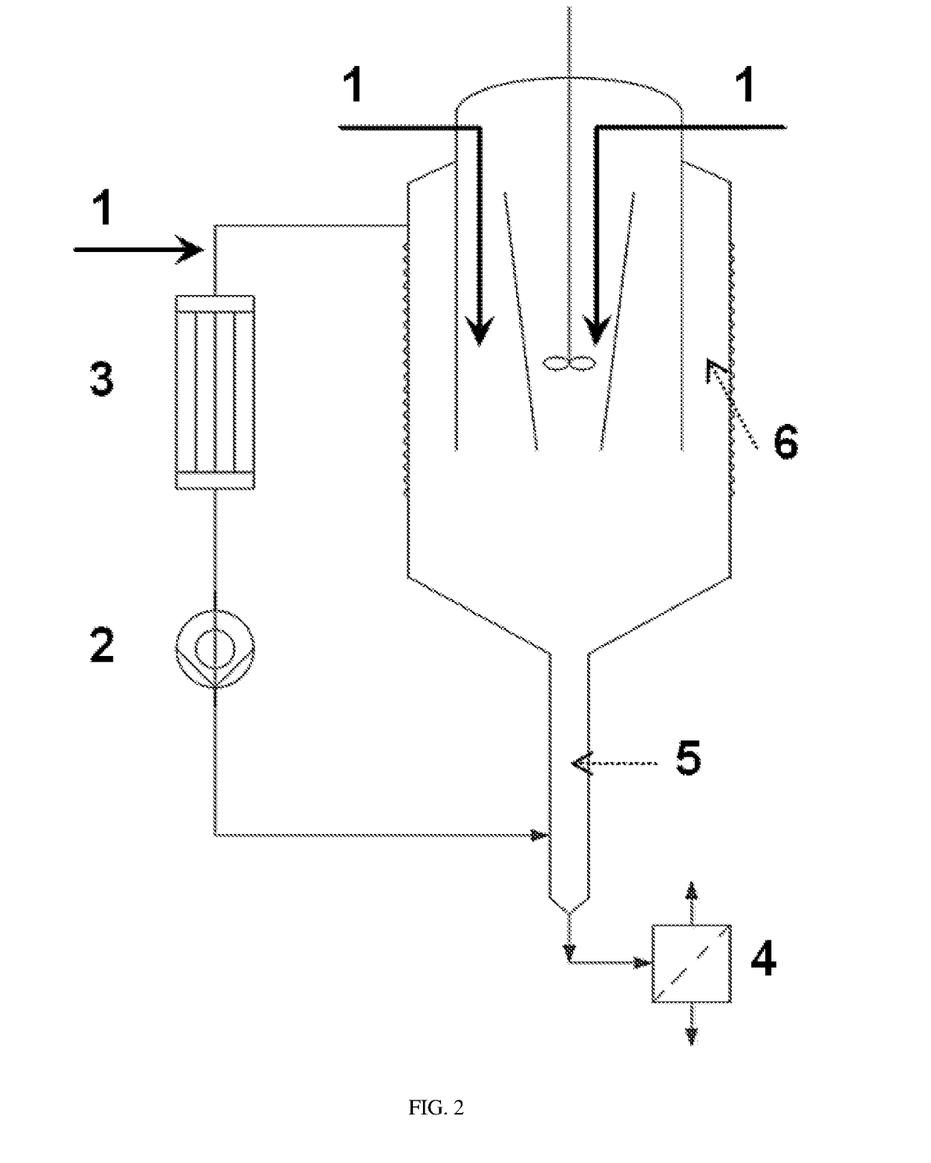
FIG. 2 illustrates a crystallizer with forced circulation and fittings, with a pumping loop at the side of the elutriator. This crystallizer comprises (1) feeding devices for fermentation broth or acid, (2) a pump or crusher, (3) a heat exchanger, (4) a solid/liquid separation (e.g. filtration) system, (5) elutriator, and (6) a calming zone.
Figure 3:
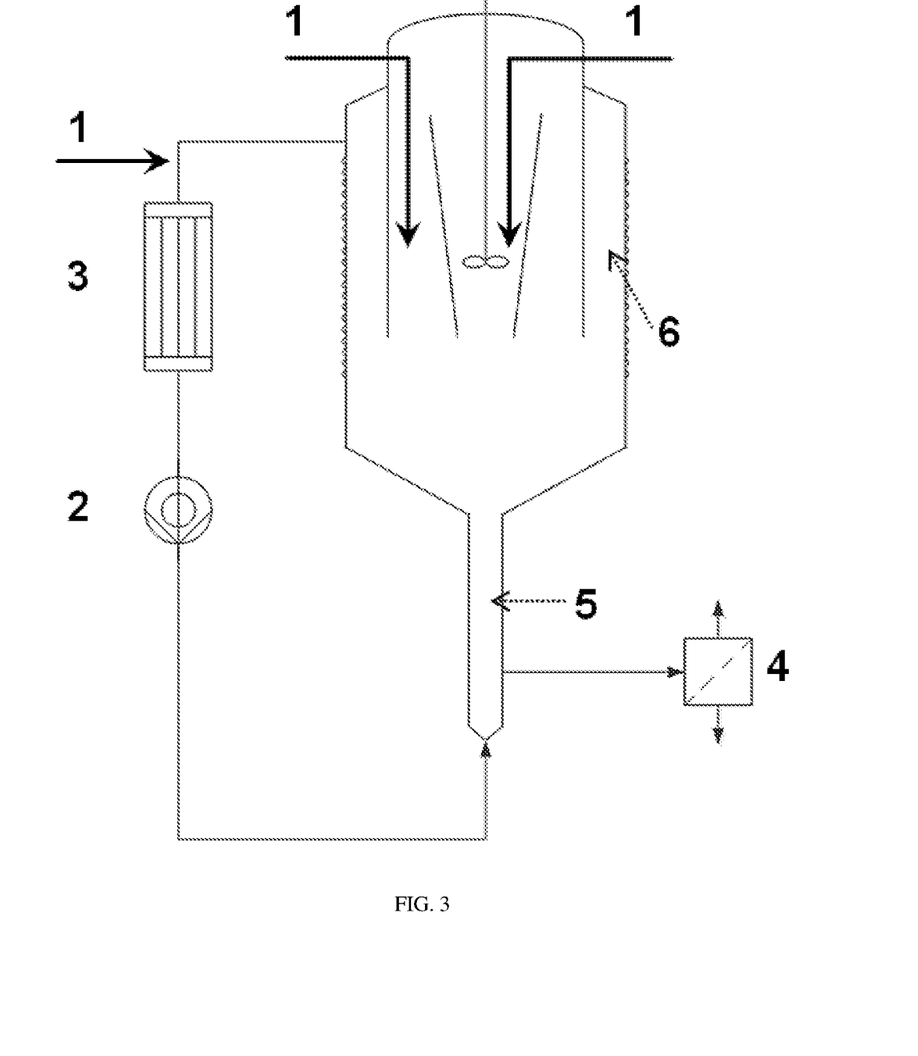
FIG. 3 illustrates a crystallizer with forced circulation and fittings, with the pumping loop at the elutriator base for whirling. This crystallizer comprises (1) feeding devices for fermentation broth or acid, (2) a pump or crusher, (3) a heat exchanger, (4) a solid/liquid separation (e.g. filtration) system, (5) elutriator and (6) a calming zone.

Possible as reactor in step (III) are customary configurations of chemical reactors that are familiar to a person skilled in the art. By way of example, mention may be made of stirrer tanks or forced circulation crystallizers such as those of the "Oslo type". Possible reactors for step (III) (also called "crystallizers") are depicted in the attached drawings:

FIG. 1 shows a crystallizer with forced circulation crystallization without fittings. Meaning of the symbols: (1) Possible feeding devices for fermentation broth or acid, (2) pump or crusher, (3) heat exchanger, (4) solid/liquid separation system (e.g., filtration).

FIG. 2 shows a crystallizer with forced circulation crystallization and fittings, with the pumping loop being used at the side of the elutriator. Meaning of the symbols: (1) Possible feeding devices for fermentation broth or acid, (2) pump or crusher, (3) heat exchanger, (4) solid/liquid separation system (e.g., filtration), (5) elutriator, (6) calming zone.

FIG. 3 shows a crystallizer with forced circulation crystallization and fittings, with the pumping loop being used at the elutriator base for whirling. Meaning of the symbols: (1) Possible feeding devices for fermentation broth or acid, (2) pump or crusher, (3) heat exchanger, (4) solid/liquid separation system (e.g., filtration), (5) elutriator, (6) calming zone.

It has been found effective, in step (III), to feed the fermentation broth and the acid to the reactor via feeding devices spaced apart (as far as possible). What is achieved as a result is that the reactants are mixed as thoroughly as possible with the reactor contents before the acid-base reaction takes place (cf. for example, Beckmann, *Crystallization*, Wiley 2013, pages 175 to 176). Possible as feeding devices are, for example, pipelines, preferably having stop valves. In one embodiment, the feeding device for the fermentation broth and the feeding device for the acid are arranged on opposite points of the reactor wall (substantially) at a right angle thereto. In another embodiment, the feeding device for the fermentation broth and the feeding device for the acid are arranged (substantially) in parallel to the reactor wall, with the feeding devices facing each other and being situated very close to, more particularly immediately on, the reactor wall.

It is possible for the reactor used in step (III) to be divided by suitable fittings into chambers. Possible resulting chambers are the calming zones (6) or elutriators (5) that are depicted in FIG. 2 and FIG. 3. Through selection of stirrer geometry and stirrer operating mode, it is possible to set the flow direction. It is likewise possible to provide the reactor with an external pumping loop, with, in this case, one of the two reactants—fermentation broth or acid—being added to the pumping loop and the other being added directly to the reactor (cf. the drawings). If a reactor is being operated with elutriator and pumping loop, the pumping loop is used at the elutriator base for whirling or at the side of the elutriator.

It has further been found effective, in step (III), with continuous performance of said step, to feed the acid at such a metering rate and the fermentation broth at such a metering rate to the reactor and to withdraw a suspension of product (i.e., aminobenzoic acid suspended in acidified fermentation broth [=mother liquor]) from the reactor at intervals or in a continuous manner, preferably in a continuous manner, such that a residence time of the suspension in the reactor from ¼ h to 10 h, preferably from ¼ h to 2 h, arises. A continuous performance of step (III) is, in the context of the present invention, understood to mean a mode in which acid and fermentation broth are continuously added to the reactor from step (III) and product (i.e., aminobenzoic acid suspended in acidified fermentation broth [=mother liquor]) is withdrawn from the reactor at least at intervals (semicontinuous mode) or preferably likewise in a continuous manner (fully continuous mode).

In a discontinuous performance of step (III), it is preferred to carry out the acid treatment in step (III) over a period from ¼ h to 10 h, preferably from ¼ h to 2 h. A discontinuous performance of step (III) is, in the context of the present invention, understood to mean a mode in which all reactants are added to the reactor and reacted therein for a desired period. After completion of step (III), the precipitated aminobenzoic acid is then isolated from the reaction mixture obtained (step (IV); see below for details). The aminobenzoic acid is thus gained in this embodiment in a batchwise manner.

Irrespective of the mode (continuous or discontinuous), the exact operating parameters (inter alia) are determined by the desired crystal size, which can be set by the residence time/reaction time and the degree of oversaturation (large crystal sizes are favored by long residence times/long reaction times and low degrees of oversaturation).

The presence of seed crystals of aminobenzoic acid during the acid treatment of step (III) can be realized as follows:

In one embodiment of the invention, the presence of seed crystals of aminobenzoic acid in step (III) is achieved by the fermentation broth and the acid being added to a suspension of seed crystals that has been initially charged in the reactor. Said seed crystals can originate from an earlier production batch or an external source. Said embodiment is especially suitable if step (III) is being carried out discontinuously. It can, however, also be applied in the start-up of a continuously performed precipitation of aminobenzoic acid in step (III) of the process according to the invention. Preferably, in both cases, a suspension of the seed crystals in a portion of the fermentation broth obtained in step (I) or step (II)(1) or step (II)(2) is used as suspension, with the seed crystals preferably being suspended in 1.0% by mass to 20% by mass of the fermentation broth used altogether in step (III).

Preferably, step (III) of the process according to the invention is carried out continuously, as defined above. In this embodiment, it is preferred, for the start-up of the continuously performed precipitation of aminobenzoic acid by acid treatment in step (III) of the process according to the invention, to initially charge in the reactor a suspension of seed crystals, to which the fermentation broth and the acid are then continuously added. After that, aminobenzoic acid starts to precipitate, it being possible for the pH to serve as control variable for the precipitation rate. Once the precipitation of aminobenzoic acid in the reactor from step (III) has started, the in situ precipitated crystals of the aminobenzoic acid act as seed crystals for the precipitation of further aminobenzoic acid. In this embodiment of the invention, the presence of seed crystals of aminobenzoic acid in addition to the seed crystals possibly initially charged for the start-up in step (III) is thus preferably achieved by fermentation broth and acid being added continuously to the reactor and a suspension of aminobenzoic acid being withdrawn from the reactor at intervals or in a continuous manner, preferably in a continuous manner, with the feeding of fermentation broth and acid and also the withdrawal of suspension being set such that, in the part of the reaction mixture that is present in the reactor (i.e., in the part of the reaction mixture that is not currently being withdrawn), crystals of aminobenzoic acid, which act as seed crystals, are always present. Preferably, the feeding of fermentation broth and acid and also the withdrawal of suspension are set such that the amount of aminobenzoic acid withdrawn via the outputted suspension within one period corresponds to the amount of aminobenzoic acid newly precipitated within the same period. The continuous generation of crystallization seeds by secondary seed formation that is necessary for a continuous procedure can be achieved by any of the known methods familiar to a person skilled in the art; for example, by collisions using a stirrer or by pumping (cf. also Beckmann, Crystallization, Wiley 2013, pages 203 to 233). The details depend on the actual design of the reactor from step (III) (of the "crystallizer") and on the desired crystal size; possibly, an elutriation is required. An elutriation can be achieved with the aid of an elutriator or hydrocyclone. In the case of a continuous procedure, the initial charging of seed crystals from an external source—additionally bought or from an earlier production batch—is thus at most necessary during the start-up; it is not necessary and not preferred, during the continuously performed precipitation of the aminobenzoic acid, to permanently feed seed crystals from such an external source. If the initial charging of seed crystals for the start-up is dispensed with, the time required until the attainment of a stationary operating state increases; in addition, the stability of the operation may be adversely affected. Although not preferred, such a procedure is, however, not ruled out.

Irrespective of the embodiment chosen, the proportion of seed crystals, if present, initially charged in suspension in step (III) in the process according to the invention is preferably set to a value from 0.50% by mass to 30% by mass, based on the total mass of the aminobenzoic acid to be precipitated in step (III). This applies to all isomers of the aminobenzoic acid. As total mass of the aminobenzoic acid to be deposited in step (III), the mass of the aminobenzoic acid at 100% deposition is, for simplification, taken as a basis for this purpose. This is revealed in a simple manner from the known use concentrations and use amounts.

The process according to the invention is preferably used for the preparation of ortho-aminobenzoic acid or of a corresponding aminobenzoic acid derivative. It is especially preferred that the seed crystals, if present, initially charged in the suspension in step (III) consist, to an extent of at least 90%, preferably to an extent of at least 95%, based on the total mass of all seed crystals initially charged in the suspension, of the form I modification, according to the nomenclature described in Ojala, W. H.; Etter, M. C., *J. Am. Chem. Soc.* 1992, 114, 10288-10293. This brings about a preferred crystallization of this modification, resulting in an increase in yield.

Step (IV), the isolation of the aminobenzoic acid precipitated in step (III), is known per se from the prior art and is achieved according to the invention preferably by filtration or centrifugation. Preferably, said step is carried out as described in WO 2015/124687 A1. In this connection, reference is made in particular to WO 2015/124687 A1, page 17, line 13 to page 17, line 16. The filtration can be carried out at reduced pressure, ambient pressure or elevated pressure. In the case of continuous performance of step (III), step (IV) is also preferably carried out continuously, i.e., the suspension withdrawn at intervals or in a continuous manner in step (III) is directly isolated at intervals or in a continuous manner following step (III).

The optional step (V), the further purification of the aminobenzoic acid gained in step (IV), is known per se from the prior art (see especially WO 2015/124687 A1 and in particular to WO 2015/124687 A1, page 18, line 4 to page 18, line 6) and is achieved according to the invention preferably by one or more washes using aqueous wash media, more particularly water. To avoid losses in yield, the pH of the aqueous wash medium can be set to the same level as in step (III) after completed addition of acid; i.e., in this embodiment, washing is carried out not with water, but with a diluted acid, more particularly the same acid as used in step (III). The product remaining after removal of the aqueous wash medium by filtration, possibly supported by application of a reduced or elevated pressure, generally has, as a result of large crystal sizes, a residual moisture which is so low that it is possible to dispense with complicated further drying steps before the further use. If step (V) is dispensed with, the same applies to the product obtained after step (IV).

The aminobenzoic acid gained according to the invention is preferably further converted to an aminobenzoic acid derivative, i.e., step (VI) is preferably carried out. Selected further conversions of the obtained aminobenzoic acid in step (VI) are:
(VI-1) Decarboxylation to form aniline;
(VI-2) Decarboxylation followed by acid-catalyzed reaction with formaldehyde to form di- and polyamines of the diphenylmethane series;
(VI-3) Decarboxylation followed by acid-catalyzed reaction with formaldehyde, followed by reaction with phosgene to form di- and polyisocyanates of the diphenylmethane series;
(VI-4) Conversion to an azo compound, more particularly to an azo dye;
(VI-5) Conversion to amides;
(VI-6) Conversion to conductive polymers such as, in particular, polyanthranilic acid.

The decarboxylation of aminobenzoic acid, more particularly of the ortho isomer, to form aniline (VI-1) is known per se and can be carried out in the context of the present invention just as described in the literature. Suitable procedures are, for example, described in WO 2015/124686 A1 and WO 2015/124687 A1. The decarboxylation is preferably carried out at a temperature in the range from 150° C. to 250° C., particularly preferably in the range from 160° C. to 220° C., very particularly preferably in the range from 180° C. to 200° C. The decarboxylation can be effected purely thermally, but also can be run catalytically. Suitable catalysts are, for example, zeolites.

The further reaction of the thus obtained aniline with formaldehyde to form di- and polyamines of the diphenylmethane series (VI-2) is likewise known per se and can be carried out according to any process in the prior art. The continuous or, in some cases, discontinuous preparation of di- and polyamines of the diphenylmethane series from aniline and formaldehyde is, for example, disclosed in EP 1 616 890 A1, U.S. Pat. No. 5,286,760, EP-A-451442 and WO-A-99/40059. The reaction takes place under acid catalysis. A suitable acid catalyst is preferably hydrochloric acid.

The further reaction of the thus obtained di- and polyamines of the diphenylmethane series with phosgene to form di- and polyisocyanates of the diphenylmethane series (VI-3) is likewise known per se and can be carried out according to any process in the prior art. Suitable processes are, for example, described in EP 2 077 150 B1, EP 1 616 857 A1, EP 1 873 142 A1, and EP 0 314 985 B1.

The conversion of the aminobenzoic acid obtained according to the invention to azo compounds, more particularly to azo dyes (VI-4) can be carried out according to any process in the prior art. By way of example, reference may be made to the known preparation of methyl red or indigo (Per Wiklund et al., *Current Organic Synthesis*, 2006, 3, 379-402).

The conversion of the aminobenzoic acid obtained according to the invention to amides (VI-5) can likewise be carried out according to any process in the prior art. By way of example, mention may be made of the primary amine of anthranilic acid (2-aminobenzylamide), which is used inter alia as starting material for the preparation of pharmaceuticals (Per Wiklund et al., *Current Organic Synthesis*, 2006, 3, 379-402).

The conversion to conductive polymers such as, in particular, polyanthranilic acid is, for example, described in Bhavana Guptaa et al., *Polymers Advanced Technologies*, 2011, 22, 1982-1988.

EXAMPLES

In all the examples, the fermentation broth used in each case was prepared by fermentation of recombinant *Corynebacterium glutamicum* ATTC 13032 strains which have a deletion or reduced expression of the trpD gene, which encodes anthranilate phosphoribosyltransferase—as described in WO 2015/124687 A1, in particular to page 6, lines 8 to 28 and example 3 (corresponds to step (I) of the process according to the invention). To deplete the microorganism used, the fermentation broth was filtered (step (II) of the process according to the invention).

Example 1

Comparison: Discontinuous Performance of the Acid Treatment Addition of Hydrochloric Acid to Initially Charged Fermentation Broth Without Seed Crystals 100 g of a fermentation broth having a content of ortho-aminobenzoic acid of 91 g/L and a pH of 6.9 were initially charged in a vessel with plane-ground joint and set to a pH of 3.6 over 1 h using hydrochloric acid having a proportion by mass of 10%. For this purpose, 29.2 g of the hydrochloric acid were necessary, corresponding to an equivalence ratio of 1.1 (corresponds, apart from the missing seed crystals, to step (III) of the process according to the invention).

After a stirring time of 1 h, the crystallizate was isolated by filtration (step (IV) of the process according to the invention) and washed with water (step (V) of the process according to the invention).

The filter resistance was $\alpha = 5.3 \cdot 10^{+10}$ 1/m$^2$, the residual moisture in the cake was 30.7% and the isolated yield was 88%. The crystal size was, on the basis of microscopic images, estimated at 200 μm.

The crystallizate was present in modification II, this being disadvantageous owing to the higher solubility thereof in comparison with modification I. The crystallizate content of ortho-aminobenzoic acid was 93%.

Example 2

Comparison: Discontinuous Performance of the Acid Treatment Addition of hydrochloric Acid to Initially Charged Fermentation Broth Without Seed Crystals In one variation of example 1, a 37% strength hydrochloric acid was used.

The filter resistance was determined at $\alpha=5.0 \cdot 10^{-10}$ l/m², the residual moisture in the cake was 61% and the isolated yield was 85%. The crystal size was, on the basis of microscopic images, estimated at 100 μm.

The crystallizate was present in modification II. The crystallizate content of ortho-aminobenzoic acid was 94%; the ash content was 0.55%.

Example 3

Comparison: Discontinuous Performance of the Acid Treatment Addition of Hydrochloric Acid to Initially Charged Fermentation Broth Without Seed Crystals In another variation of example 1, the hydrochloric acid was added over 5 min.

The filter resistance was determined at $\alpha=4.9 \cdot 10^{-10}$ l/m², the residual moisture in the cake was 46.7% and the isolated yield was 93%. The crystal size was, on the basis of microscopic images, estimated at 150 μm.

The crystallizate was present in modification II.

Example 4

Inventive: Discontinuous Performance of the Acid Treatment Continuous Feeding of Hydrochloric Acid and Fermentation Broth to a Suspension of Seed Crystals In the so-called fed-batch process, hydrochloric acid and fermentation broth were metered continuously to an initially charged suspension of seed crystals of modification I in fermentation broth having a pH of 3.5. The fermentation broth (both the initially charged and the fed broth) had a content of ortho-aminobenzoic acid of 91 g/L, the hydrochloric acid had a content by mass of 17%. The metering was carried out over 2 h, with the pH being between 2.3 (briefly at the start of the metering) and 3.5 (over the entire remainder of the metering time) (step (III) of the process according to the invention).

After a stirring time of 1 h, the crystallizate was isolated by filtration (step (IV) of the process according to the invention) and washed with water (step (V) of the process according to the invention).

The filter resistance was determined at $\alpha=6 \cdot 10^{-10}$ l/m², the residual moisture in the cake was 30.5% and the isolated yield was 89%. The crystal size was, on the basis of microscopic images, estimated at 400 μm.

The crystallizate was present in modification I. The crystallizate content of ortho-aminobenzoic acid was 98.5%; the ash content was 0.03%.

Example 5

Semicontinuous Performance of Step (III) Continuous Feeding of Hydrochloric Acid and Fermentation Broth, Withdrawal of Suspension at Intervals, to a Suspension of Seed Crystals Example 5 was carried out like example 4 with the difference that not only were the reactants fermentation broth and hydrochloric acid metered continuously, but also suspension was withdrawn at intervals, this approaching a fully continuous mode. The reactants hydrochloric acid and fermentation broth were metered such that there was a residence time of the crystals in the reactor of about 45 min. The pH varied between 3.2 and 3.5. Every 15 min, suspension was withdrawn (in each case, 60 ml for 200 ml total batch size) and characterized.

The residual moisture in the filter cake was 1% and the isolated yield was 91%. The crystal size was, on the basis of microscopic images, estimated at 400 μm.

The crystallizate was present in modification I. The crystallizate content of ortho-aminobenzoic acid was 99%; the ash content was 0.02%.

The invention claimed is:

1. A process for preparing ortho aminobenzoic acid or an ortho aminobenzoic acid derivative, comprising:
   (I) fermenting a raw material with microorganisms, said raw material comprising at least one fermentable carbon-containing compound, wherein an ortho aminobenzoate- and/or an ortho aminobenzoic-acid-comprising fermentation broth is obtained and wherein the fermenting is carried out at a pH of ≥6.5 to prevent spontaneous precipitation of ortho aminobenzoic acid in the fermentation broth;
   (II) optionally, pretreating the fermentation broth obtained in (I), said pretreatment comprising
      (1) removing the microorganisms from the fermentation broth obtained in (I) without pH adjustment, wherein a microorganism-depleted fermentation broth is obtained, and/or
      (2) decoloring the fermentation broth obtained in (I) or, when carrying out (II) (1), the microorganism-depleted fermentation broth obtained in (II) (1), without pH adjustment;
   (III) treating the fermentation broth obtained in (I) or (II) (1) or (II) (2), in one-step with acid in a reactor to precipitate ortho aminobenzoic acid from the fermentation broth;
   (IV) isolating the ortho aminobenzoic acid precipitated in (III), wherein mother liquor remains;
   (V) optionally further purifying the ortho aminobenzoic acid from (IV);
   (VI) optionally further converting the ortho aminobenzoic acid obtained in (IV) or (V) to form an ortho aminobenzoic acid derivative;
   wherein (III) is carried out in the presence of seed crystals of ortho aminobenzoic acid for increasing the yield of ortho aminobenzoic acid, and the presence of the seed crystals of ortho aminobenzoic acid is achieved such that the fermentation broth and the acid are added to a suspension of the seed crystals that has been initially charged in the reactor, in which at least 90% of the seed crystals initially charged in the suspension, based on the total mass of all seed crystals initially charged in the suspension, are the polymorph form I of ortho aminobenzoic acid.

2. The process as claimed in claim 1, in which the treating the fermentation broth with acid in (III) is carried out such that the pH of the resulting mixture corresponds to that of the isoelectric point of ortho aminobenzoic acid.

3. The process as claimed in claim 1, in which the acid used in (III) comprises hydrochloric acid, sulfuric acid and/or phosphoric acid.

4. The process as claimed in claim 3, in which the acid used in (III) is a mixture of hydrochloric acid and a portion of the mother liquor obtained in (IV).

5. The process as claimed in claim 1, in which, in (III), the fermentation broth and the acid are fed to the reactor via feeding devices spaced apart.

6. The process as claimed in claim 1, wherein (III) is performed continuously or discontinuously,
   wherein the continuous performance of (iii) comprises feeding of the acid at such a metering rate and feeding the fermentation broth at such a metering rate to the reactor and withdrawing a suspension of ortho amnion benzoic acid in the mother liquor from the reactor at intervals or in a continuous manner, such that a residence time of the suspension in the reactor from ¼ hr to 10 hr arises;
   or
   wherein the discontinuous performance of (III) comprises treating with acid in one-stage over a period of from ¼ hr to 10 hr.

7. The process as claimed in claim 1, in which the microorganisms in (I) comprise at least one of *Escherichia coli*, *Pseudomonas putida* and *Corynebacterium glutamicum*.

8. The process as claimed in claim 7, in which the microorganisms in (I) comprise *Corynebacterium glutamicum* ATTC 13032.

9. The process as claimed in claim 1, in which the suspension of seed crystals is a suspension of the seed crystals in a portion of the fermentation broth obtained in (I) or (II), wherein the seed crystals are suspended in 1.0% by mass to 20% by mass of the fermentation broth used altogether in (III).

10. The process as claimed in claim 1, in which (III) is carried out discontinuously.

11. The process as claimed in claim 1, in which (III) is carried out continuously and the presence of seed crystals of ortho aminobenzoic acid in (III) is achieved such that fermentation broth and acid are added continuously to the reactor and a suspension of ortho aminobenzoic acid in mother liquor is continuously withdrawn from the reactor, wherein the feeding of fermentation broth and acid and also the withdrawal of suspension are set such that, in the part of the reaction mixture that is present in the reactor, crystals of ortho aminobenzoic acid are always present.

12. The process as claimed in claim 1, in which (VI) is carried out and comprises one of the following conversions:
   (VI-1) decarboxylating said ortho aminobenzoic acid to form aniline;
   (VI-2) decarboxylating said ortho aminobenzoic acid, followed by acid-catalyzed reaction with formaldehyde to form di- and polyamines of the diphenylmethane series;
   (VI-3) decarboxylating said ortho aminobenzoic acid, followed by acid-catalyzed reaction with formaldehyde, followed by reaction with phosgene to form di- and polyisocyanates of the diphenylmethane series;
   (VI-4) converting said ortho aminobenzoic acid to an azo compound;
   (VI-5) converting said ortho aminobenzoic acid to amides;
   (VI-6) converting said ortho aminobenzoic acid to conductive polymers.

13. The process of claim 1, in which the carbon-containing compound in (I) comprises at least one of starch hydrolysate, sugarcane juice and sugar beet juice.

14. The process of claim 1, in which in (III), the pH of the resultant mixture is set to a level in the range of from 3.0 to 4.7.

* * * * *